United States Patent [19]

Davies et al.

[11] Patent Number: 5,342,949

[45] Date of Patent: Aug. 30, 1994

[54] 2 STEP PROCESS FOR PREPARING BIOLOGICALLY ACTIVE TROPANE DERIVATIVES AND STARTING MATERIAL THEREFORE

[75] Inventors: Huw M. L. Davies, Clemmons; Elie Saikali; Steven R. Childers, both of Winston-Salem, all of N.C.

[73] Assignee: Wake Forest University, Winston-Salem, N.C.

[21] Appl. No.: 977,535

[22] Filed: Nov. 17, 1992

Related U.S. Application Data

[62] Division of Ser. No. 851,090, Mar. 13, 1990, Pat. No. 5,262,428.

[51] Int. Cl.$^5$ ............................................. C07D 451/02
[52] U.S. Cl. .................................................. 546/124
[58] Field of Search ........................... 546/124; 514/304

[56] References Cited

U.S. PATENT DOCUMENTS 3,120,537  2/1964  Archer et al. ...................... 546/124
3,813,404  5/1974  Clarke et al. ...................... 546/124

OTHER PUBLICATIONS

Boja, et al., "New Potent Cocaine Analogs: Ligand Binding and Transport Studies in Rat Striatum", *European Journal of Pharmacology*, 184 (1990) 329–332.

Carroll, et al., "Synthesis, Ligand Binding, QSAR and CoMFA Study of 3β-Carbixylic Acid Methyl Esters", *Journal of Medicinal Chemistry*, vol. 34, No. 9 (1991), p. 2719–2725.

Clarke, et al., "Compounds Affecting the Central Nervous System.4. 3β-Phenyltropane-2-Carboxylic Esters and Analogs", *Journal of Medicinal Chemistry*, vol. 16, No. 11 (1973) pp. 1260–1267.

"Synthesis of (±)-Ferruginine and (±)-Anhydroecgonine Methyl Ester By a Tandem Cyclopropanation/-Cope Rearrangement", *J.Org.Chem.*, vol. 56, No. 19 (1991) p. 5696–5700.

Madras, et al. "Cocaine Receptors Labeled by [$^3$H]2β-(4-Fluorophenyl Tropane", *Molecular Pharmacology*, 36:;518–524 (1989).

Davies, et al., "Novel Entry to the Tropane System by Reaction of Rhodium (II) Acetate Stabilized Vinylcarbenoids with Pyrroles", *Tetrahedron Letters*, vol. 30, No. 35, pp. 4653–4656 (1989).

Davies et al., "Chemistry of Vinylcarbenoids with a Single Electron Withdrawing Group. An Approach to Tropane Alkaloids" American Chemical Society, Dec. 5–7, 1990, pp. 181–182.

*Primary Examiner*—Alan L. Rotman
*Attorney, Agent, or Firm*—Zarley, McKee, Thomte, Voorhees, & Sease

[57] ABSTRACT

Preparation of biologically active tropane derivatives of novel configurations. The compounds are prepared by decomposing vinyldiazomethanes in the presence of pyrroles to provide a bicyclic ring containing the basic tropane ring system which is then reacted with an aryl Grignard reagent in the presence of a copper (I) or (II) salt to provide 3-aryl-tropane derivatives.

16 Claims, 1 Drawing Sheet

2 STEP PROCESS FOR PREPARING BIOLOGICALLY ACTIVE TROPANE DERIVATIVES AND STARTING MATERIAL THEREFORE

GRANT REFERENCE

This invention was made with government support under R01-DA-06301-02 awarded by the National Institute of Drug Abuse. The government has certain rights in the invention.

This is a divisional of copending application Ser. No. 07/851,090 filed on Mar. 13, 1992 now U.S. Pat. No. 5,262,428.

BACKGROUND OF THE INVENTION

Cocaine has the following formula:

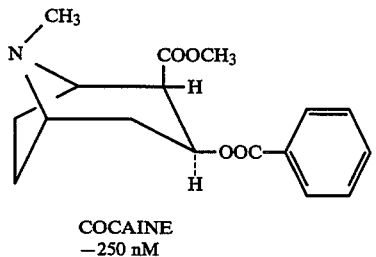

COCAINE
−250 nM

The basic ring structure of cocaine is a tropane ring system. Thus, in preparing cocaine analogs, this tropane ring system must be preserved.

The illicit use of cocaine represents the one of the most significant problems of drug abuse in modern society. In the United States, researchers estimate that at least 20 million people have used this drug at some point in their lifetimes. One of the biggest problems with cocaine use is its high addictive liability. Cocaine is a potent activator of brain reward systems, and people who take the drug are generally highly motivated to maintain the same effect.

The mechanism of cocaine action involves its ability to block dopamine uptake into neurons by inhibiting the neuronal dopamine transporter. This uptake process is one of the most important ways in which dopamine actions are normally terminated in the central nervous system. Thus, administration of cocaine acts to increase dopamine levels, especially in those areas of the brain which activate reward (or pleasure) centers. By measuring the affinity of cocaine analogs in binding to brain dopamine transporters in brain membranes, researchers have been able to predict the relative potencies of these analogs in producing cocaine-like behavioral actions, see Ritz, M. C. and Kuhar, M. J.: J. Pharmacol, Exp. Ther. 248, 1010–1017 (1989). Another important pharmacological characteristic of cocaine is its rapid kinetic properties. Cocaine has an extremely rapid onset of action, and its CNS effects are quickly finished. There is no question that these rapid kinetics contribute to the high incidence of repetitive use of cocaine (e.g., "binges") which are common among addicts.

Despite the advances in understanding cocaine actions, there is as yet no pharmacological strategy that has been effective in treating cocaine addicts. Historically, in the field of drug abuse, there have been three general strategies employed to decrease drug self-administration. It is important to consider how the synthesis of novel cocaine analogs would fit in with these general approaches.

The first approach is replacement drugs. In this strategy, an analog which produces the same effect as the abused drug is given to the addict as a safer alternative. A classic example is methadone maintenance for heroin addicts. By providing an orally-acting drug which replaces heroin, this program seeks to eliminate the problems of intravenous drug use. Synthesis of novel cocaine analogs may be relevant in this approach in at least two different ways. First, compounds which are active orally may be developed. Second, analogs may be developed which are metabolically stable but with slower kinetics of action. Such analogs would be useful in the initial stages of treatment of cocaine addiction, where an analog may substitute for cocaine and thus reduce craving, but act slow enough not to produce the "rush" of euphoria that is such an important component in cocaine addiction.

The second approach is antagonist drugs. In this approach, analogs which actually block the effects of the abused drug are given to the addict. An example is the use of naloxone as an opioid antagonist. Naloxone is especially useful in the treatment of heroin overdose, where it can specifically block the lethal effect of heroin or morphine. In the case of cocaine, however, it is difficult to devise a chemical strategy for producing specific antagonists for at least two reasons. First, little is known about the structure of the cocaine binding site. Therefore, it is imperative that a more complete knowledge of cocaine structure-activity relationships can be obtained so that rational pharmacology can begin to devise effective blocking agents. Synthesis of novel cocaine analogs is vital in establishing this important database. A second reason it is difficult to identify cocaine antagonists is the fact that cocaine binds to the dopamine transporter instead of traditional neurotransmitter receptors. The dopamine transporter is a molecule which acts much more like an enzyme rather than a receptor. Therefore, the chemical strategy for designing drugs to block cocaine at the transporter site is very different than a strategy involving conventional receptors. One potential approach is to synthesize compounds which would act allosterically at the dopamine transporter and thereby modify cocaine binding.

The third approach is punishment drugs. In this strategy, an analog is used to produce undesirable side effects of its own when it is taken in conjunction with the abused drug. A well-known example of such a system is disulfuram (Antabuse ®), which produces toxic reactions when taken together with alcohol.

The lack of available significant analogs of cocaine has hampered the significant development of drugs to be used in all three approaches of treatment, namely, replacement drugs, antagonist drugs, and punishment drugs. There is therefore a real and continuing need for the development of a synthesis procedure for cocaine analogs which allow the synthetic chemist to quickly, conveniently and economically develop "tailor made" cocaine analogs. They can then be systematically tested for their suitability as replacement drugs for cocaine, as antagonist drugs for use in cocaine therapy, and for punishment drugs for use in cocaine therapy.

Perhaps the main problem with the original approaches to development of cocaine derivatives as used in the art, see for example Clark, et al., Journal of Medicinal Chemistry, 1973, 16,1260; and Clark, et al., U.S. Pat. No. 3,813,404 issued May 28, 1974, is that this original approach uses as a starting material cocaine itself, which therefore limits synthetic flexibility. There is therefore a continuing need for a broader approach to synthesis of cocaine analogs which enables a wider range of cocaine derivatives to be prepared. In this manner, the molecule of cocaine itself can be explored by varying structural moieties on the molecule and the precise mechanism of cocaine action, including precise knowledge about the structure of the cocaine binding site, can be obtained.

Accordingly, it is a primary object of the present invention to provide a novel synthesis process for cocaine analogs which does not use cocaine as its starting material.

Another primary objective of the present invention is to provide a process for development of cocaine analogs which can be investigated for their use as replacement drugs in cocaine therapy, as antagonist drugs for use in cocaine therapy, and as punishment drugs for use in cocaine therapy.

A still further objective of the present invention is to provide a wide range of cocaine derivatives which can be systematically used and tested for a chemical strategy for producing specific knowledge of the cocaine structure-activity relationship, so that a rational pharmacological approach can be obtained to devising effective blocking agents.

A yet further objective of the present invention is to provide novel pharmacologically active 3-aryltropane derivatives which have potent activity in binding assays substantially higher than known cocaine analogs, thus allowing the compounds to effectively mediate the effect of cocaine by binding to the dopamine transport site in the brain.

The method and manner of accomplishing each of the above objectives, as well as others, will become apparent from the detailed description of the invention which follows hereinafter.

SUMMARY OF THE INVENTION

Figure 1:
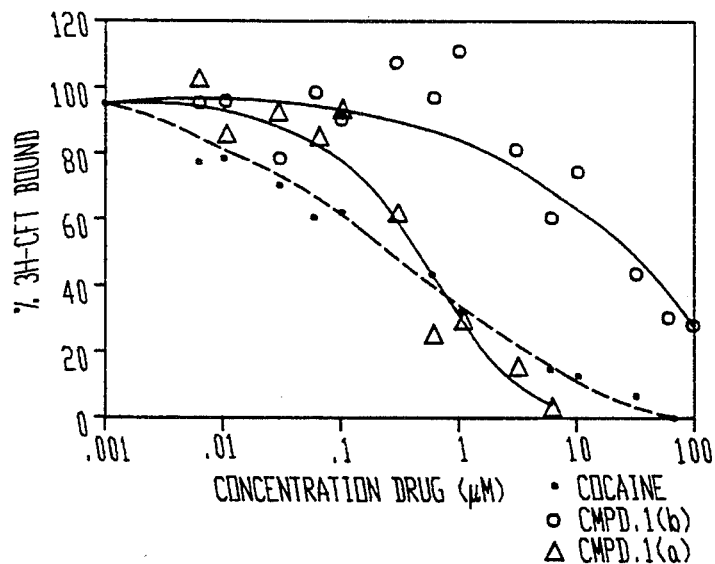
FIGS. 1, 2 and 3 show how various cocaine analogs prepared herein compare with cocaine itself in binding to the dopamine transport site and in comparison with a known potent tropane analog [³H]CFT.

In the process of the present invention 3-aryltropane derivatives are prepared by reacting 8-azabicyclo[3.2.1]oct-2-ene with an aryl Grignard reagent in the presence of catalytically effective amounts of copper (I) and/or copper (II) salts. The 3-aryl-tropane derivative starting material can be conveniently prepared by decomposing functionalized vinyldiazomethanes in the presence of certain pyrroles, preferably in substantial excess of the stoichiometric amount, using a decomposition catalyst, preferably a rhodium catalyst. The catalyst may also be a copper, palladium or silver salt catalyst. This provides a bicyclic intermediate containing the basic tropane ring system which is thereafter converted to an 8-azabicyclo[3.2.1]oct-2-ene, which itself may be used as a starting material to react with an aryl Grignard reagent in providing the synthesis route to the unique cocaine analogs of the present invention.

DETAILED DESCRIPTION OF THE INVENTION

The starting material of the present invention, namely the 8-azabicyclo[3.2.1]oct-2-ene, has the following formula:

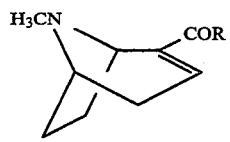

In the above formula R is selected from the group consisting of $C_1$ to $C_8$ alkyl and $C_1$ to $C_8$ oxyalkyl. In other words, the two position moiety may be functionally substituted by ketone groups or ester groups.

Two of the present inventors, namely Dr. Huw M. L. Davies, and Mr. Saikali have previously published concerning the general synthesis used for the starting material of the present invention, namely synthesizing 8-azabicyclo[3.2.1]oct-2-ene of the above formula. In this regard see, Davies, et al., "Novel Entry to the Tropane System by Reaction of Rhodium (II) Acetate Stabilized Vinylcarbenoides with Pyrroles," Tetrahedron Letters, vol. 30, no.35, pp. 4653–4656, (1989) a December 1990 abstract of a regional ASC meeting held in New Orleans, entitled Davies, et al., "Chemistry of Vinylcarbenoides with a Single Electron Withdrawing Group, an Approach to Tropane Alkyloids", American Chemical Society, Dec. 5–7, 1990, pp. 181–182; Davies, et al., "Synthesis of ± Ferruginine and Anhydroecgonine Methyl Ester by a Tandem Cyclopropanation/Cope Rearrangement", Journal of Organic Chemistry, 1991, Vol. 56, pp. 5696–5700. The subject matter of each of these publications of Davies et al is incorporated herein by reference and therefore need not be described in full detail. However, certain preferred process operations, not specifically mentioned in the above articles, are described herein for sake of completeness.

Preparation of the starting material for the Grignard addition of the present invention, namely, preparation of 8-azabicyclo[3.2.1]oct-2-ene as above described employs in its first step a process of decomposing of a functionalzed vinyldiazomethane of the formula:

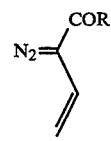

in the presence of at least a stoichiometric amount of a pyrrole of the formula:

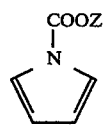

wherein Z is a functional group protector, and also in the presence of a small but effective amount of a decomposition catalyst selected from the group consisting of rhodium, copper, palladium and silver salts, to provide an intermediate bicyclic compound.

R as shown above represents a $C_1$ to $C_8$ alkyl or $C_1$ to $C_8$ oxyalkyl. Preferrably R is an alkyl and therefore as explained herein after, the resulting analog of cocaine ultimately prepared will have a ketone group at the two position. In the pyrrole, Z represents a functional group protector such as trimethylsilylethyl, although it is understood that other classic protecting groups such as tertiarybutyl group may also be employed.

The amount of the pyrrole for this first reaction scheme needs to be at least a stoichiometric amount in comparison with the vinyldiazomethane and preferrably is in excess of the stoichiometric amount, perhaps within the range of a two-fold to a five-fold excess. An excess is preferred in terms of achieving the desired high yields of the bicyclic intermediate because the vinyldiazomethane is decomposed to a very reactive intermediate, namely a vinylcarbenoid which will, unless it is trapped by use of stoichiometric excesses of the pyrrole, rapidly decompose.

The pyrroles above described can be conventionally prepared using well known chemistry as described in the Journal of Organic Chemistry, 1991, vol. 56 article, of the author earlier cited. The reaction is preferably run at a temperature of within the range of from 25° C. to about 100° C., preferrably at about 80° C. The reaction can be run at 25° C. if there is slow addition of the vinyldiazomethane to the pyrrole. The pressure is not critical in this reaction step.

As explained above, the reaction is conducted in the presence of a decomposition catalyst selected from the group consisting of rhodium, copper, palladium and silver salts. Preferrably the catalyst is a rhodium salt catalyst and may be a rhodium (II) acetate, mandelate, trifluoroacetate, hexanoate, pivalate or octanoate. The presently most preferred catalyst is rhodium octanoate which seems to allow higher yields of desired product. The amount of catalyst may vary from 0.25 mole percent to about 2.0 mole percent of the vinyldiazomethane, and is preferrably about 1.0 mole percent of the amount of the vinyldiazomethane reactant.

Reaction time does not appear to be critical and the time may vary from a few minutes up to several hours if drop wise addition is accomplished. The other carbon atoms of the 8-azabicyclo [3.2.1]oct-2-ene can include substituents other than hydrogen (e.g. one or more of the other carbon atoms of the bicyclic system can include a lower alkyl substituent group) because a more highly substituted pyrrole or vinyldiazomethane may be used as starting material.

This first step reaction produces an intermediate bicyclic compound which upon hydrogenating, removal of the deprotective group and reductive methylation is converted to the earlier described 8-azabicyclo]3.2.-1]oct-2-ene. The hydrogenation, deprotecting and reductive methylation are all well known steps and need not be described herein.

Where R equals methyl and the protecting group used is trimethylsilyl the intermediate is methyl 8-(2-(trimethylsilyl)ethoxycarbonyl)-8-azabicyclo[3.2.1]octa-2,6-dien-2-oate.

This reaction is preferrably conducted in the presence of a solvent and the solvent is preferrably a non-polar solvent. Suitable non-polar solvents for conducting this reaction may be pentane, hexane, and benzene. Other suitable non-polar solvents, capable of dissolving the basic reactants may also be employed, with the precise solvent not being critical, as long as it is in fact non-polar.

For details of the hydrogenating, deprotecting and reductive methylation see, the previously incorporated by reference 1991 vol. 56, Journal of Organic Chemistry article. There it is basically described that the catalytic hydrogenation is a process employing a Wilkinson's catalyst and that deprotection occurs with, for example, tertiarybutyl ammonium flouride to give the desired 8-azabicyclo[3.2.1]oct-2-ene at yields as high as 95%. As explained in the earlier referenced article, the composition is purified by silica gel column chromatography.

The 8-azabicyclo[3.2.1]oct-2-ene is then used as a starting material for the process of the present invention. It has been found that the 8-azabicyclo[3.2.1]oct-2-ene formula earlier described, can be converted to biologically active cocaine analogs having a wide variety of active analog structures by reacting with a aryl Grignard reagent in the presence of a catalytically effective amount of a copper salt catalyst. The copper salt catalyst may be a copper (I) or copper (II) catalyst.

As previously described, it is preferred that the R group of the 8-azabicyclo[3.2.1]oct-2-ene be $C_1$ to $C_8$ alkyl, rather than an oxyalkyl since it is preferred that the two substituent be a ketone substitution rather than an ester substitution. The ketones behave better in the copper catalysed reaction, and as explained later in the biological activity section of the specification, should have higher metabollic stability and have equivalent binding site activity. The Grignard addition reaction is run in a suitable non-polar organic solvent, preferrably ether or tetrahydrofuran.

The Grignard reagent (ArMgX) may be any suitable aryl magnesium halide. The aryl group may be phenyl, substituted phenyl, $C_1$ to $C_8$ alkylaryl, polyaryl such as anthracyl or alkylpolyaryl. Alkyl magnesium halides ($C_1$ to $C_8$) may also be used. The "X" moiety represents a halide group and is preferably bromide. The copper salt may be a copper (I) or (II) salt and can be, for example, copper bromide dimethyl sulfide. The amount of the Grignard reagent is preferably an excess of the stoichiometric amount in order to assure completion of the reaction. Suitable high yields are obtained when an excess of up to four-fold of the Grignard reagent is employed. The amount of the copper salt catalyst can be from 5% (molar) to 20% (molar) of the Grignard reagent, and is preferably 15 mole percent of the amount of the Grignard reagent. The reaction to produce the desired ketone is represented by the following equation reaction:

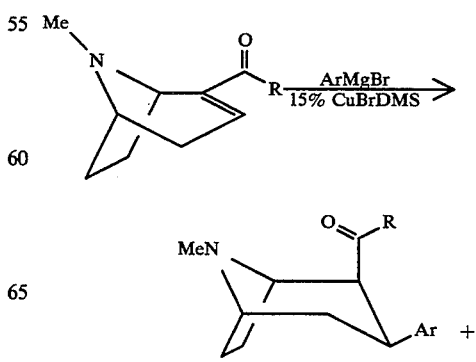

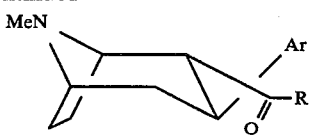

As seen the reaction product is a mixture of two structural isomers, one with the 2-moiety position upwardly (a) and the second with the 2-moiety position downwardly. (b) Those analogs that are most preferred are the analogs wherein R is alkyl and therefore the two position moeity is a ketone moiety, and that the structural isomer is with the ketone groups in an up position. These are far more active in binding assays, than the downward structural isomers and in some instances as much as 200 times more active in site-binding.

Certain other process conditions are worthy of mention. The reaction is not temperature critical and may be run at anything from 0° C. or lower up to room temperature, or even higher. The reaction is preferably run under an inert gas atmosphere. The reaction is substantially immediate and therefore may be run from a few minutes to as much as twelve hours. Preferably the reaction occurs under stirring in order to assure completeness. After completion the reaction can be quenched with for example HCl ice, with the desired compound extracted with ether. It may be purified as illustrated in the examples by conventional silica gel chromatogrpahy.

The compounds may be administered orally, parenterally or intravenously. The preferred route of administration is oral. The dose levels may be from 4 micrograms per kilogram of body weight up to 50 milligrams/kg of body weight and more typically from 20 micrograms/kg up to 15 mg/kg.

The following examples are offered to further illustrate but not limit both the process of the invention and as well to demonstrate the highly efficient binding capability in membrane assays of the compounds of the present invention, as measured by their $IC_{50}$ values in comparison with cocaine and other well known site-binders.

The $IC_{50}$ refers to the concentration of the compound that inhibits 50 percent of the binding. The less of the compound needed that is the lower the $IC_{50}$, the more effective the compound at mediating the effect of cocaine. The presence of keto functionality is preferred since it is more stable and not as easy to break down as the ester group. The biological activity examples illustrate that those compounds of the present invention that are structural isomers with the two substituted keto functionality in the "up" structural isomer position are by far the most potent compounds and offer the most significant potential for mediating the effects of cocaine. Some of these isomers are up to as many as 200 times more potent than the down position keto groups.

EXAMPLES 1-6

TABLE 1

| Examples | R | Ar | Yield % a (up) | b (down) |
|---|---|---|---|---|
| 1 | CH₃ | —C₆H₄—H | 77 | 1.3 |
| 2 | CH₃ | —C₆H₄—F | 73 | 1.5 |
| 3 | CH₃ | —C₆H₄—CH₃ | 79 | 2.3 |
| 4 | CH₃ | —C₆H₄—CH₂CH₃ | 88 | 1.7 |
| 5 | CH₃ | naphthyl | 82 | 0.7 |
| 6 | CH₂CH₃ | —C₆H₄—CH₃ | 95 | 1.7 |

PREPARATIONS FOR EXAMPLES 1-6 OF TABLE 1

Example 1

2α-Acetyl-8-methyl-3β-phenyl-8-azabicyclo[3.2.1]octane (1a) and

2β-Acetyl-8-methyl-3β-phenyl-8-azabicyclo[3.2.1]octane (1b)

A solution of phenylmagnesium bromide (0.80 mL, 2.44 mmol, 3 M in ether) was added to a dry CuBr. DMS dimer (0.0750 g, 0.37 mmol) under argon atmosphere. The mixture was stirred for 15 minutes at room temperature and then cooled to 0° C. after the addition of dry THF (5 mL). A solution of ferruginine (0.10 g, 0.61 mmol) in dry THF (2 mL) was added and the mixture was stirred for 4 hours at 0° C. and then stirred overnight. The reaction was quenched with conc. HCl/ice (10 mL) at 0° C., extracted with ether (2x). The aqueous layer was made basic with conc. NH₄OH/ice at 0° C., extracted with CH₂Cl₂ (3x), dried (Na₂SO₄) and then concentrated under reduced pressure. Purification on silica gel column chromatography (9/1 ether/triethylamine-8.75/0.25/1 ether/methanol/triethylamine) afforded 1a and 1b (0.104 g, 77%).

1a: 33%; IR (neat) 2934,1708,1600,784,760 cm⁻¹;¹H NMR (CDCl₃) δ7.20(m,5H),3.36 (m,1H), 3.32(dd,1H,J=11.6,2.4 Hz), 3.23(m,1H),3.11(dt,1H,J=5.7,11,8 Hz), 2.36(s,3H),2.00(m,1H), 1,85(s,3H),1,80(m,3H),1.58(m,2H);¹³C(CDCl₃)δ208.1,1-43.3, 127.9,127.3,125.9,62.5,61.1,58.2,39.8,38.5,35.7,30.3,26.0, 22.2; MS m/z (rel intensity) 243(37),200(72), 172(12),159(3), 128(8),115(9),96(68),82(100),55(10),HRMS calcd for C₁₆H₂₁ON: 243,1632,found 243.1621.

1(b): 44%; IR (neat) 2940,1710,1680,1600,750,690 cm$^{-1}$; $^1$H NMR (CDCl$_3$) δ7.27-7.12(m,5H),3.50(d.1H,J=6.6 Hz),3.36(m,1H),3.00 (m,2H),2.54(ddd,1H,J=2.7,12.3,12.3 Hz), 2.25(s,3H),2.21(2.3H), 2.30-2.00(m,3H),1.65-1.79(m,2H); $^{13}$C (CDCl$_3$)δ208.1,143.2 128.0,127.1,125.7,64.5,62.4,60.1,42.1,34.0,33.7,30.1,26.4, 25.2; MS m/z (rel intensity) 243(33),200(78), 172(13),143(7), 128(7),115(7),96(71),82(100),55(7),HRMS calcd for C$_{16}$H$_{21}$ON 243.1623, found 243.1624.

Example 2

2α-Acetyl-8-methyl-3β-(p-fluorophenyl)-8-azabicyclo[3.2.1]oct-ane (2a) and
2β-Acetyl-8-methyl-3β-(p-fluorophenyl)-8-azabicyclo[3.2.1]octane (2b)

A solution of p-fluorophenylmagnesium bromide (0.53 mL, 1.05 mmol, 2M in ether) was added to a dry CuBr. DMS dimer (0.0325 g, 0.16 mmol) under argon atmosphere. The mixture was stirred for 15 minutes at room temperature and then cooled to 0° C. after the addition of dry THF (5 mL). A solution of ferruginine (0.0436 g, 0.26 mmol) in dry THF (2 mL) was added and the mixture was stirred for 4 hours at 0° C. and then stirred overnight. The reaction was quenched with conc, HCl ice (10 mL) at 0° C., extracted with ether (2x). The aqueous layer was made basic with conc, NH$_4$OH/ice at 0° C., extracted with CH$_2$Cl$_2$(3x), dried (Na$_2$SO$_4$) and then concentrated under reduced pressure. Purification on silica gel column chromatography (9/1 ether/triethylamine-8.75/0.25/1 ether/methanol/-triethylamine)afforded 2a and 2b (0.05 g, 73%).

2a: 29%; IR (neat) 2940,1700 1600 840 810 cm$^{-1}$;$^1$H NMR (CDCl$_3$)δ7.25-6.86(m,4H),3.36(m,1H),3.25(m,2H), 3.12(dt, 1H,J=11.6,5.6 Hz),2.41(s,3H),1.94(s,3H),1.51-2.10(m,6H); $^{13}$C NMR (CDCl$_3$) δ208.5,163.7,159.2,139.5,129.3,129.1,115.4, 114.9,62.9,61.5,59.1,40.1,38.9,35.2,30.5,26.3,22.5; MS m/z (rel intensity) 261(39),218(74),190(11),177(3),146(6),133(5), 97(89),82(100),55(4),HRMS calcd for C$_{16}$H$_{20}$ONF: 261.1529, found 261.1531.

2(b): 44%; IR (neat) 2940,1700,1680,1600,800,790 cm$^{-1}$;$^1$H NMR(CDCl$_3$) δ7.00-7.14(m,4H),3.49(m,1H),3.34(m,1H), 2.91(m,2H), 2.50(ddd,1H,J=12.3,12.3,2,8 Hz),2.19(s,3H),1.96(s,3H),2.20-2.03(m,1H),1.70-1.50(m,4H); $^{13}$C NMR (CDCl$_3$) δ207.7,163.4,158.6, 138.8,128.7,128.5,114.9,114.5,64.4,62.4,60.1,42.1,34.2,3-3.4, 29.9,26.3,25.2; MS m/z (rel intensity) 261(38),218(80), 190(17),161(7),146(8),133(9),97(100),82(62),55(11); HRMS calcd for C$_{16}$H$_{20}$ONF: 261,1529, found 261.1533.

Example 3

2α-Acetyl-8-methyl-3β-[p-tolyl]-8-azabicyclo[3.2.1]octane (3a) and
2β-Acetyl-8-methyl-3-β-[p-totyl]-8-azabicyclo[3.2.1]octane (3b)

A solution of p-tolylmagnesium bromide (1.0 mL, 0.99 mmol, 1M in ether) was added to a dry CuBr,DMS dimer (0.0306 g, 0.15 mmol) under argon atmosphere. The mixture was stirred for 15 minutes at room temperature and then cooled to 0° C. after the addition of dry THF (5 mL). A solution of ferruginine (0.0410 g, 0.25 mmol) in dry THF (2 mL) was added and the mixture was stirred for 4 hours at 0° C. and then stirred overnight. The reaction was quenched with conc. HCl ice (10 mL) at 0° C., extracted with ether (2x). The aqueous layer was made basic with conc. NH$_4$OH/ice at 0° C., extracted with CH$_2$Cl$_2$(3x), dried (Na$_2$So$_4$) and then concentrated under reduced pressure. Purification on silica gel column chromatography (9/1 ether/triethylamine-8.75/0.25/1 ether/methanol/triethylamine) afforded 3a and 3b (0.005 g, 79%).

3a: 24%; IR (neat) 2940,1710,1500,800,720 cm$^{-1}$;$^1$H NMR (CDCl$_3$δ7.11(d,2H,J=8.2 Hz),7.03 (d,2H,J=8.2 Hz),3.33(m,1H),3.23 m,2H),3.08(dt,1H,J=11.7,11.7,5.3 Hz), 2.25(s,3H),2.40(s.3H),2.10 −1.75(m,4H),1.91(s,3H),1.70-1.50(m,2H);$^{13}$C NMR(CDCl$_3$)δ208.3, 140.0,135.1,128.7,126.9,64.6,62.4, 60.2,42.1,34.2,33.3,30.2,26. 4,25.2,20.9; MS m/z (rel intensity)257(41), 214(66),186(11), 157(4),142(5),128(6),96(73),82(100),55(10);HRMS calcd for C$_{17}$H$_{23}$ON 257.1779, found 257.1773.

3b: 55%; IR (neat) 2920,1705,1680,1500,800,790 cm$^{-1}$;$^1$H NMR (CDCl$_3$) δ7.12 (d,2H,J=8.3 Hz), 7.05(d.2H,J=8.3 Hz), 3.48(d,1H,J=6.8 Hz), 3.35(m,1H),2.96(m,2H), 2.52(ddd, 1H, J=12.2,12.3,2.8 Hz), 2.27(s,3H),2.20(s,3H), 1.97(s,3H),2.20-2.01 (m,1H),1.70-1.50(m,4H); −C NMR (CDCl$_3$) δ208.3,140.0, 135.1,128.7,126.9,64.6,62.4,60.2,42.1,34.2,33.3,30.2, 26.4, 25.2,20.9; MS m/z (rel intensity) 257(33), 213(68),186(12), 157(4),139(7),115(7),97(100),96(72),94(12),83 (77),82(99), 55(3); HRMS calcd for C$_{17}$H$_{23}$ON 257.1779, found 257.1782.

Example 4

2α-Acetyl-8-methyl-3β-(p-ethylphenyl)-8-azabicyclo[3.2.1]octane (4a) and
2β-Acetyl-8-methyl-3β-(p-ethylphenyl)-8-azabicyclo[3.2.1]octane 4(b). A solution of p-ethylphenylmagnesium bromide (excess in ether) was added to a dry CuBr.DMS dimer (0.284 g, 1.382 mmol) under argon atmosphere. The mixture was stirred for 15 minutes at room temperature and then cooled to 0° C. A solution of ferruginine (0.0761 g, 0.461 mmol) in dry ether (2 mL) was added and the mixture was stirred for 4 hours at 0° C. and then stirred overnight. The reaction was quenched with conc. HCl ice (10 mL) at 0° C., extracted with ether (2x). The aqueous layer was made basic with conc. NH$_4$OH/ice at 0° C., extracted with CH$_2$Cl$_2$(3x), dried (Na$_2$SO$_4$) and then concentrated under reduced pressure. Purification on silica gel column chromatography (9/1 ether/triethylamine-8.75/0.225/1 ether/methanol-triethylamine) afforded 4a and 4b (0.11 g, 88%).

4a: 33%, IR (neat) 2910,1700,1500,690 cm$^{-1}$;$^1$H NMR (CDCl$_3$) δ7.01(d,2H,J=8.3 Hz),6.93(d,2H,J=8.3 Hz),3.22(m,1H), 3.17(dd,1H,J=11.7,2.2 hz),3.09(m,1H),2.97(dt,1H,J=57,11.6 Hz),2.44(1,2H,J=7.7 Hz),2.28(s,3H),2.01(m,1H),1.81(m,3H),1.79(s,3H 1.52(m,2H),1.06(t,3H,J=7.7 Hz); $^{13}$C (CDCl$_3$) δ208.9, 142.1, 141.0, 127.0,127.6, 62.9,61.5, 58.8,40.0,38.9,35.6,30.7,28.3,26.3,22.6, 15.7; MS m/z (rel intensity) 271(27),228 (59), 200(7),171(3),143(3),128(6),97(96),82(100),55(18), HRMS calcd for $C_{18}H_{25}ON$: 271.1936, found 271.1938.

4b: 55%; IR (neat) 2940,1710,1680,810,700 cm$^{-1}$;$^1$H NMR (CDCl$_3$) δ7.13(d.2H,J=8.3 Hz),7.06(d,2H, J=8.3 Hz),3.46 (q,1H,J=7.0 Hz),3.34(m,1H),2.94(m,2H),2.56(q,2H,J=7.6 Hz),2.55(m,1H),2.19(s, 3H),2.11(m,1H),1.96(s,3H),1.64 (m,3H),1.14(t,3H,J=7.6 Hz),1.19(t,1H,J=7.6 Hz); (CDCl$_3$) δ208.3,141.5,140.2,127.5, 126.9,64.5, 62.4,60.1,42.1,34.1,33.4,30.2,28.3,26.4,25.2,15.5

Example 5

2α-Acetyl-8-methyl-3β-[1-naphthyl]-8-azabicyclo[3.2.1]octane (5a) and 2β-Acetyl-8-methyl-3β-[1-naphthyl]-8-azabicyclo[3.2.1]octane 5b). A solution of 1-naphthylmagnesium bromide (excess in ether) was added to a dry CuBr.DMS dimer (0.1866 g, 0.9078 mmol) under argon atmosphere. The mixture was stirred for 15 minutes at room temperature and then cooled to 0° C. A solution of ferruginine (0.05 g, 0.3026 mmol) in dry ether (2 mL) was added and the mixture was stirred for four hours at 0° C. and then stirred overnight. The reaction was quenched with conc. HCl ice (10 mL) at 0° C., extracted with ether (2x). The aqueous layer was made basic with conc. NH$_4$OH/ice at 0 ° C., extracted with CH$_2$Cl$_{12}$(3x), dried (Na$_2$SO$_4$ and then concentrated under reduced pressure. Purification on silica gel column chromatography (9/1 ether/triethylamine-8.75/0.25/1 ether/methanol/triethylamine) afforded 5a and 5b (0.0727 g, 82%).

5a: 47%; IR (neat) 2920,1690,1650,1590,780,770 cm$^{-1}$;$^1$H NMR (CDCl$_3$) δ7.40-7.30(m,7H),4.09(m,1H),3.68(d,br,1H,J=10.7 Hz), 3.49(d,1H,J=4.3 Hz),3.30(m,1H), 3.26(m, 1H),2.46(s,3H),2.31-2.21(m,2H), 1.98(s,3H), 1.91-1.72(m,3H); MS m/z(rel intensity) 293(44),250(100),220(20),193(11),165 (15),141(9),97(45), 82(88),55(12).

5b: 35%; IR (neat) 2940,1705,1680,1590,790,770 cm$^{-1}$;$^1$H NMR (CDCl$_3$) δ7.97-7.24(m,7H),3.76(dt,1H,J=12.9,4.8), 3.75 (m,1H), 3.50(m,1H),3.17(m,1H),2.92(ddd,1H,J=2.9,12.6,12.6 Hz), 2.26(s,3H),1.84(s,3H),2.50-1.93(m,2H),1.61(dt,1H,J=3.8, 12.1 Hz),1.19 (t,1H,J=7.0 Hz), 1.01(t,1H,J=7.1 Hz): $^{13}$C (CDCl$_3$) δ207.1, 137.4,133.8, 131.3, 129.3,126.7,126.1,125.7, 125.5,124.8,122.4,64,64.5,62.8,58.3,42.2,34.7,30.8,29.9,26.7, 25.3; Ms m/z (rel intensity) 293(45),250(100),193(7),178(7), 165(14),152(12), 141(8),97(52),82(13),55(5),HRMS calcd for $C_{20}H_{23}NO$ 293.1779, found 293.1774.

Example 6

2α-Ethylcarbonyl-8-methyl-3β-[p-tolyl]-8-azabicyclo[3.2.1]octane (6a) and 2β-Ethylcarbonyl-8-methyl-3β-[p-tolyl]-8-acabicyclo[3.2.1]octane (6b).

A solution of p-tolylmagnesium bromide (2.23 mL, w.we mmol, 1M in ether) was added to a dry CuBr.DMS dimer (0.0689 g. 0.3347 mmol) under argon atmosphere. The mixture was stirred for 15 minutes at room temperature and then cooled to 0° C. after the addition of dry ether (5 mL). A solution of 3-ethylcarbonyl-8-azabicyclo[3.2.1]oct-2-ene (0.10 g, 0.5578 mmol) in dry ether (2 mL) was added and the mixture was stirred for four hours at 0° C. and then stirred overnight. The reaction was quenched with conc. HCl ice(10 mL) at 0° C., extracted with ether (2x). The aqueous layer was made basic with conc. NH$_4$OH/ice at 0° C., extracted with CH$_2$Cl$_2$(3x), dried (Na$_2$SO$_4$) and then concentrated under reduced pressure. Purification on silica gel column chromatography (9/1 ethertriethylamine-8.75/0.25/1 ether/methanol/triethylamine) afforded 6a and 6b (0.144 g, 95%).

6a: 35%: IR (neat) 2920,1700,1660,790,810 cm$^{-1}$;$^1$H NMR (CDCl$_3$) β 7.09(d,2H,J=8.3 Hz),7.02(d,2H,J=8.1 Hz),3.25(m,1H), 3.22(m,1H),3.20(dd,1H,J=11.2,2.7 Hz),3.09(dt,1H, J=11.2,5.6 Hz),2.39(s,3H),2.25(s,3H),1.98(dq,2H,J=14.0,7.3 Hz),2.12-1.80(m,4H), 1.56(dd,1H, J=5.3,3.0 Hz),1.61(m,1H),0.79(t,3H,J=7.3 Hz); $^{13}$C NMR (CDCl$_3$) δ 211.4,140.8,135.7,129.1,127.6,63.2,61.5, 58.1, 40.1,38.9,36.6, 35.8,26.4,22.5,20.9,7.4.

6b: 60%: IR (neat) 2920,1710,1500,800,750 cm$^{-1}$;$^1$H NMR (CDCl$_3$ δ 7.09(d.2H,J=8.3 Hz), 7.03(d,2H,J=8.3 Hz),3.45(d,1H, J=6.3 Hz),3.36(m,1H),2.97(m,1H), 2.90(t,1H,J=5.2 Hz),2.55(td,1H, J=12.3,2.8 Hz),2.26(s,3H),2.19(s,3H),2.31-2.10(m,2H), 2.05 (m,1H), 1.78-1.52(m,3H),0.83(t,3H,J=7.2 Hz); $^{13}$C NMR (CDCl$_3$ δ 210.3, 140.2,1134.9,128.7,126.9,64.6,62.4,59.4,42.1,35.2,34.4 33.5, 26.4,25.3,20.9,7.8.

EXAMPLES OF BIOLOGICAL ACTIVITY

[$^3$H]CFT binding is performed in rat striatal membranes according to published methods (Madras, B. K., Spealman, R. D., Fahey, M. S., Neumeyer, J. L., Saha, J. K. and Milius, R. A.: Mol. Pharmacol. 36, 518–524 (1989)). Dopamine transport sites are labeled in striatum using 0.3 nM [3H]CFT (New England Nuclear), with 30 μM (−)cocaine to define non-specific binding. Crude membranes are isolated from striatum, and washed twice before resuspension in fresh Tris buffer (100 mM NaCl, 50 mM tris-HCl,pH 7.4 at 4°). Membranes (final volume: 0.6 ml) are incubated in Tris buffer with [3H]CFT and various unlabeled ligands for 2 hours at 4°. Bound radioactivity is determined by rapid filtration through GF/B glass fiber filters (presoaked in Tris buffer containing 0.1% bovine serum albumin). Norepinephrine transport sites are determined with 4 nM [3H]mazindol, with membranes prepared from frontal cortex, and 5 μM desmethylimipramine is used to define nonspecific binding (Javitch, J., Blaustein, R. O. and Snyder, S. H., Eur. J. Pharmacol. 90, 461–463 (1983), and Javitch, J. A., Blaustein, R. O. and Snyder, S. H.: Mol. Pharmacol. 26, 35–44 (1984)). Serotonin transport sites are labeled with 0.2 nM [3H]paroxetine (Habert, E., Graham, D., Tahraoui, L., Clautre, Y. and Langer, S. Z., Eur. J. Pharmacol. 118, 107–111 (1985)), using membranes from rat brainstem and 1 μM citalopram to define non-specific binding.

In a typical competition experiment, various concentrations of the novel compounds are added to assay tubes; a similar displacement curve using unlabeled cocaine is used as a control. Preliminary Ki values are calculated using the Cheng-Prusoff equation (Yamaura, H. I., Enna, S. J. and Kuhar, J. J., eds., Neurotransmitter Receptor binding (Raven Press, N.Y.), 2nd ed., 1985). For compounds with moderate to high affinity, curves will be analyzed to fit either one or two site models by the LIGAND curve fitting program.

Since cocaine is a competitive inhibitor of dopamine transport, some analogs with interesting biological properties may be allosteric inhibitors of transport. Such compounds may have the ability to block the actions of cocaine without blocking dopamine transport. The possibility that compounds are allosteric inhibitors of the dopamine transport site is screened initially by single-point determinations of dissociation of [$^3$H]CFT. After [$^3$H]CFT binding has reached equilibrium (2 hr at 4°), an excess of an unlabeled compound is added to initiate dissociation. Competitive inhibitors will not alter the $t_{\frac{1}{2}}$ of [$^3$H]CFT dissociation, while allosteric inhibitors should produce significant changes in $t_{\frac{1}{2}}$. Assay of binding at the normal time of $t_{\frac{1}{2}}$ after initiation of dissociation should be a rapid method to indicate non-competitive behavior. (If such results are positive.) If a compound produces a change in Bmax instead of $K_D$ of [$^3$H]CFT binding, it may be a non-competitive inhibitor and may produce allosteric changes in the dopamine transporter.

Below are illustrated several of the analogs prepared in examples 1–6 with their IC$_{50}$ values (nM) in displacing [$^3$H]CFT binding to rat striatal membranes. The list also includes CFT itself will allow a direct comparison with standard literature. The IC$_{50}$ value of cocaine and CFT as here measured in these assays are comparable to values reported in the literature.

TABLE 2

IC$_{50}$ Value of Cocaine Analogs in comparison with Cocaine and CFT standard assay

[Structures shown:
- COCAINE —250 nM
- CFT 20 nM
- 1a —300 nM
- 1b —20,000 nM
- 2b —1000 nM
- 3a —8 nM
- 3b —2000 nM
- 4a —500 nM
- 5a 100 nM
- 6a —10 nM
- 7a —70 nM]

Figure 2:
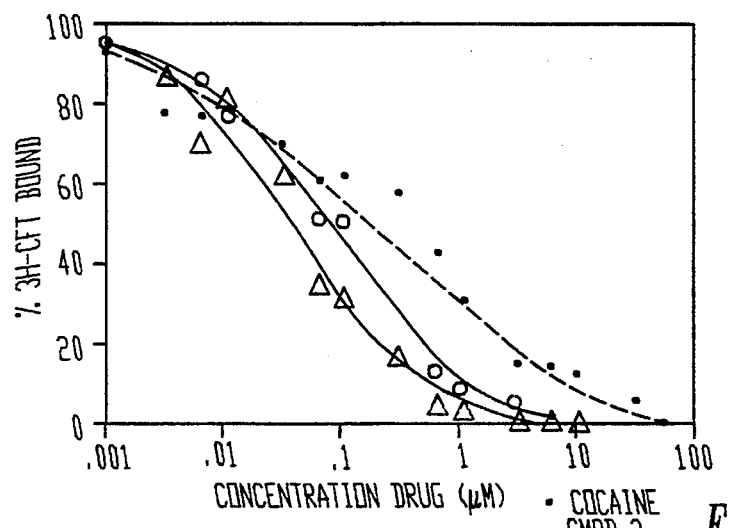
Figure 3:
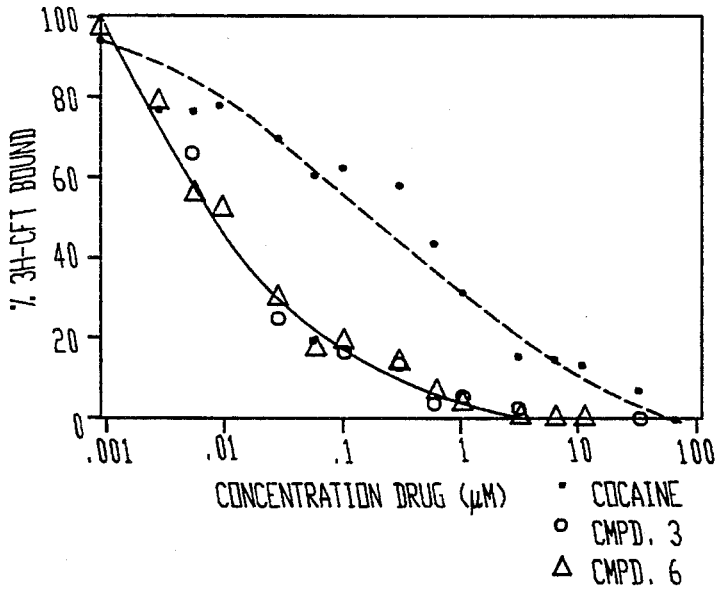

FIGS. 1, 2 and 3 show actual binding curves of several of these novel cocaine analogs to demonstrate several important points about structure-activity relationships. Many of these compounds have lost the ester groups of cocaine including the ester linkage between the phenyl and tropane rings, and the replacement of the methyl ester group with methyl or ethyl ketone derivatives). Such compounds are metabolically stable compared to cocaine, and may have very interesting pharmacokinetic properties. It is important to note that 90% of the metabolism of cocaine goes through the ester groups via plasma esterase activity. These compounds in which the ester groups have been replaced by keto, alkyl and aryl groups offer potentially greater metabolic stability. Some compounds display substantially lower IC$_{50}$ values than conventionally prepared and used cocaine analogs. In particular, FIG. 1 shows that the orientation of the ketone group is important in determining binding potency, since compound 1a (with the ketone group in the up or alpha position) is 60 times more potent than compound 1b (with the ketone in the beta position). Cocaine itself is represented by solid dots in FIG. 1, compound 1b by circles and compound 1a by triangles.

FIG. 2 shows that replacing a methylester (in CFT) with a methyl ketone (in compound 2a) has little effect on potency. Here again, cocaine is represented by dots, compound 2 by circles and CFT by triangles.

FIG. 3 shows that replacement of methyl ketone (see compound 3) with ethyl ketone (see Compound 6) has no effect on potency.

The $IC_{50}$ values in the assays listed in Table 2 demonstrate the highly potent nature of the novel analogs of the present invention in comparison with other known analogs used for possible mediation of binding effect and in comparison with the binding effect of cocaine itself. It will also demonstrate that the alpha position i.e., up for the 3-position moeity, is substantially more active than the beta position (see for example 1a in comparison with 1b), i.e. 300 nM in comparison with 20,000 nM indicating the alpha position is over 65 times more potent. Other examples, as illustrated in table 2, are even more dramatic, for example 3a and 3b where it is in excess of 200 times more active for up of alpha position moiety.

It therefore can be seen that the invention accomplishes at least all of its stated objectives.

What is claimed is:

1. A method of preparing 3-aryltropane derivatives of the formula:

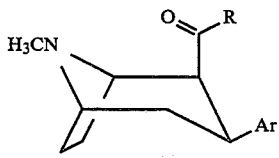

wherein R equals $C_1$ to $C_8$ alkyl and Ar is an aromatic ring moiety said aromatic ring moiety being selected from the group consisting of phenyl, substituted phenyl, said process comprising:
   (a) reacting an anhydroecgonine of the formula:

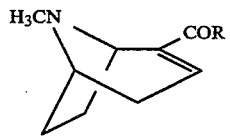

wherein R is selected from the group consisting of $C_1$ to $C_8$ oxyalkyl with an aryl Grignard reagent wherein the aryl group is selected from the group consisting of phenyl, substituted phenyl, and naphthyl in the presence of a catalytically effective amount of a copper (I or II) salt.

2. The process of claim 1 wherein the aryl Grignard has the formula ArMgX wherein X is halide.

3. The process of claim 2 wherein X is bromide.

4. The process of claim 1 wherein reaction is conducted in the presence of in excess of the stoichiometric amount of the Grignard reagent.

5. The process of claim 4 when the excess amount is up to a four-fold excess.

6. The process of claim 1 wherein the reaction is conducted in the presence of a solvent.

7. The process of claim 6 wherein the organic solvent is selected from the group consisting of ether and tetrahydrofuran.

8. A process of claim 1 wherein the copper (I) or copper (II) salt is selected from the group consisting of bromides, iodides and copper bromide dimethyl sulfide.

9. The process of claim 1 wherein the amount of copper salt is from 1% to 15% of the moler amount of the Grignard reagent.

10. The process of claim 9 wherein the amount of copper catalyst is from 5% to 15% of the mole percent basis of the Grignard reagent.

11. A method of preparing 3-aryltropane derivatives, from vinyldiazomethanes, said method comprising;
   (a) decomposing a functionalized vinyldiazomethane of the formula;

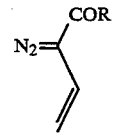

in the presence of at least a stoichiometric amount of a pyrrole of the formula:

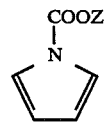

wherein Z is a functional group protector, and also in the presence of a small but effective amount of a decomposition catalyst selected from the group consisting of rhodium, copper, palladium and silver salts, to provide an intermediate bicyclic compound;
   (b) converting the bicyclic intermediate to provide an anhydroecgonine of the formula:

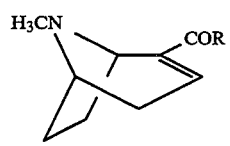

wherein R is selected from the group consisting of $C_1$ to 8 alkyl and $C_1$ to $C_8$ oxyalkyl:
   (c) reacting said anhydroecgonine of the above described formula wherein R is selected from the group consisting of $C_1$ to $C_8$ oxyalkyl with an aryl Grignard reagent wherein the aryl group is selected from the group consisting of phenyl, substituted phenyl, and naphthyl and alkylpolyaryl in the presence of a catalytically effective amount of a copper (I) or (II) salt.

12. The process of claim 11 wherein the amount of pyrrole is from about 2 times to about 5 times in excess of the stoichiometric amount.

13. The process of claim 1 wherein catalyst is a rhodium salt catalyst.

14. The process of claim 11 wherein the rhodium catalyst is present in the amount of from 0.25% to 2.0% moler weight percent basis of the amount of vinyldiazomethane.

15. The process of claim 11 wherein the catalyst is rhodium octanoate.

16. 3-ethylcarbonyl-8-azabicyclooct-2-ene.

* * * * *